United States Patent [19]

Hong et al.

[11] Patent Number: 4,622,392
[45] Date of Patent: Nov. 11, 1986

[54] THIOPHOSPHOLIPID CONJUGATES OF ANTITUMOR AGENTS

[75] Inventors: Chung I. Hong, Williamsville; Charles R. West, Amherst, both of N.Y.

[73] Assignee: Health Research Inc. (Roswell Park Division), Buffalo, N.Y.

[21] Appl. No.: 623,002

[22] Filed: Jun. 21, 1984

[51] Int. Cl.$^4$ .................. C07H 15/12; C07H 17/00
[52] U.S. Cl. .................................................. 536/29
[58] Field of Search .................. 424/180; 514/47, 48, 514/49, 51; 536/27, 28, 29

[56] References Cited

U.S. PATENT DOCUMENTS 3,937,809  2/1976  Jacobi ................................ 424/60
4,291,024  9/1981  Turcotte ............................ 424/180

FOREIGN PATENT DOCUMENTS 0671290  3/1980  U.S.S.R. ............................ 536/27

OTHER PUBLICATIONS

J. G. Turcotte et al., Cytotoxic Liponucleotide Analogs, Biochim. Biophys. Acta, 619, 604–618, 619 (1980).
Matsushita et al., Phospholipid Derivatives of Nucleoside Analogs as Prodrugs . . . , Cancer Research, 41, 2707 (1981).
Ryu et al., Phospholipid-Nucleoside Conjugates, J. Med. Chem., 25, 1322 (1982).
MacCoss et al., The Synthesis . . . and . . . Biological Evaluation of Ara C-Diphosphate-Dipalmitin, Biochem. Biophys. Res. Comm., 85, 714 (1978).
Hong et al., Synthesis and Antitumor Activity of 1-β-D-Arabinofuranosylcytosine Conjugates of Cortisol and Cortisone; Biochemical and Biophysical Research Communications; vol. 88, No. 4, Jun. 27, 1979; pp. 1223–1229.
Hong et al., Proceedings of the 73rd Meeting of the American Association for Cancer Research, Abs. No. 788 (1982).
Hong et al., Proceedings of the 13th International Cong. Chemotherapy, Part 257, 19 (1983).
Hong et al., Proceedings of the 74th Meeting of the American Association for Cancer Research, Abs. No. 1204 (1983).
Hong et al., 186th American Chemical Society National Meeting, Aug. 28–Sep. 2, 1983.
R. I. Geran et al., Cancer Chemotherapy Reports (Part 3) 3(2), 7 (1972).
R. E. Geran et al., Cancer Chemotherapy Reports (Part 3) 3(2), 47 (1972).
Berdel et al., Cytotoxicity of Thioether-Lysophospholipids in Leukemias and Tumors of Human Origin; Cancer Research, 43, 5538–5543 (1983).
Boeryd et al., Action on Various Experimental Tumour-Host Systems of Methoxy-Substituted Glycerol Ethers Incorporated into the Feed; Acta Path. Microbiol. Scand., Sect. A 88: 11–18 (1980).
Hallgren et al., Occurrence, Synthesis and Biological Effects of Substituted Glycerol Ethers; Prog. Chem. Fats Other Lipids, 46, 45–58 (1978).
Boeryd et al., Stimulation of Immune Reactivity by Methoxy-Substituted Glycerol Ethers Incorporated into the Feed; Eur. J. Immunol., vol. 8, 678–680 (1978).
Boeryd et al., The British Journal of Experimental Pathology, vol. LII (Apr. 1971), Studies on the Effect of Methoxy-Substituted Glycerol Ethers on Tumor Growth and Metastasis Formation; pp. 221–230.

Primary Examiner—Ethel G. Love
Attorney, Agent, or Firm—Christel, Bean & Linihan

[57] ABSTRACT

This invention relates to cytotoxic compounds. More particularly, this invention relates to conjugates of antitumor agents, and thiophospholipids exhibiting enhanced antitumor activity to methods for producing such compounds and to pharmaceutical compositions containing cytotoxically effective amounts of such compounds as a primary effective ingredient.

4 Claims, No Drawings

THIOPHOSPHOLIPID CONJUGATES OF ANTITUMOR AGENTS

Cancer is considered collectively as a group of diseases which can occur in any system, organ or tissue of the body. Causation of all cancers are not known nor are there any reported major qualitative differences metabolically between cancer cells and host tissue cells. Accordingly, cancer chemotherapy, unlike chemotherapy prescribed for such as infectious diseases wherein the disease-causing organism itself provides a distinct metabolic or structural target, has a far more restrictive fundamental concept upon which to pattern therapeutic treatment.

Most known classes of anticancer drugs exert their activity principally due to quantitative differences in metabolic rates of production or levels of certain nucleic acids, enzymes, proteins, hormones, metabolic intermediates, etc. rather than due to qualitative differences existent between cancer cells and normal cells. Thus, anticancer drugs do not apparently exhibit selective toxicity as toxicity is considered in the classical sense.

The usefulness of cytotoxic drugs, in the treatment of malignancy, has been severely limited by toxicity of the treating agent to normal tissue such as the rapidly proliferating cells of the bone marrow and gastrointestinal tract or myocardium, rapid catabolism to the ineffective metabolites, and clinical resistance to these agents.

In attempts to overcome the difficulties, a variety of prodrugs of anticancer or antitumor agents have been synthesized and examined for therapeutic values. Notable examples among the prodrugs which have been produced are 5'-adamantoyl, 5'-palmitoyl, and $N^4$-behenoyl derivatives of 1-$\beta$-D arabinofuranosylcytosine(ara-C). However, such compounds have been proven to be too lipophilic to be soluble in aqueous solvent systems with the result that they have been suspended in 0.9% sodium chloride solutions containing 0.5% Tween 80 surfactant or dissolved in 0.9% sodium chloride solutions with large amounts of detergent, hydrogenated castor oil polyethylene glycol ether (HCO-60) for injection.

These initial agents have been followed by prodrugs in which the nucleosides are covalently bonded to corticosteroids (Hong et al. Biochem. Biophys. Res. commun. 88, 1223, 1979), and phospholipids (M. MacCoss et al. Biochem. Biophys., Res. Commun. 85, 714, 1978; T. Matsushita et al., Cancer Res. 41, 2707, 1981; E. K. Ryu, et al., J. Med. Chem. 25, 1322, 1982; J. G. Turcotte et al., Biochim. Biophys. Acta. 619, 604 and 619, 1980). Among the ara-C/phospholipid conjugates, 1-$\beta$-D-arabinofuranosylcytosine 5'-diphosphage-L-1,2-dipalmitin (ara-CDP-L-dipalmitin) has exhibited promising therapeutic results as an anticancer compound, against intraperitoneally (i.p.) and intracerebrally (ic.) implanted L1210 lymphoid leukemia in mice (Hong et al, Proceedings of the 73rd Meeting of the Am. Assoc. Cancer Res. Abs. No. 788, 1982), with the discovery that the L form is more effective than the D isomer or the D,L racemic mixture (Hong et al. Proceed. of 13th Internat. Cong. Chemotherapy Part 257, 19, 1983).

However, the dipalmitin moiety, once liberated from the conjugate by enzymatic hydrolysis, does not have a biological activity, particularly an antitumor activity. Therefore, the phospholipid moities which have been reported to have very interesting biological activities are chosen for conjugation, which include 1-0-alkyl-2-0-palmitoyl glycerols. The 1-0-alkyl analogs of ara-CDP-L-dipalmitin have also exhibited beneficial therapeutic results when utilized to treat i.p. implanted L1210 lymphoid leukemia, including 1-$\beta$-D-arabinofuranosylcytosine 5'-diphosphate-1-0-octadecyl-2-0-palmitoyl-5N-glycerol (ara-CDP-L-PBA), the racemic mixture (ara-CDP-DL-PBA) and 1-$\beta$-D-arabinofuranosylcytosine 5'-diphosphate-rac-1-0-hexadecyl-2-0-palmitoyl glycerol (ara-CDP-DL-PCA). (Hong et al, Proceed. 74th Meeting Am. Assoc. Cancer Res. Abs. No. 1204, 1983; 186th Am. Chem. Soc. Nat. Mtg. Abs. No. MEDI 60, 1983).

The aforementioned compounds have also proven to be resistant to cytidine deaminase and very effective against partially deoxycytidine kinase deficient ara-C resistant L1210 leukemia in mice.

It is an object of the present invention to provide cytotoxic compositions of matter possessing unique and beneficial physiochemical properties.

Another objective of the present invention is to provide novel phospholipid conjugates functioning as cytotoxic agents.

A further objective of the present invention is to provide novel liponucleotide compounds which function to deliver cylotoxic agents to tumor cells.

Still a further objective of the present invention is to provide cytotoxic drugs which can form liposomes allowing penetrability of tumor cells via e.g., lysosomotropism or related membrane phenomena.

Yet another object of the present invention is to provide anticancer nucleosides releasable within the cell via phospholipid-enzyme specific reactions or nonspecific mechanisms.

These and other objectives of the present invention will become more apparent from the description which follows:

SUMMARY OF THE INVENTION

The above and other objects, features and advantages of the present invention are realized by providing compounds of the generic formula:

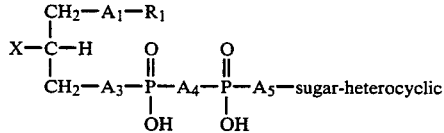

wherein:
  $R_1$ is selected from the group consisting of alkyl and alkenyl containing from about 8 to about 22 carbon atoms;
  $A_1$ is selected from the group consisting of

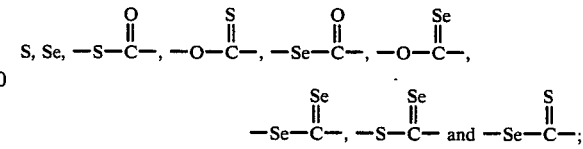

$A_3$, $A_4$ and $A_5$ are each independently selected from the group consisting of O, S, Se and —NH—; and
  X is selected from the group consisting of halogen and $R_2A_2$- wherein $R_2$ is fatty acyl containing from about 8 to about 22 carbon atoms or alkyl or acetyl containing from 1 to about 22 carbon atoms and $A_2$ is

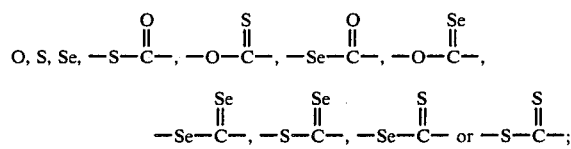

and physiologically acceptable salts thereof.

The sugar moiety, preferably selected from ribose, deoxyribose, lyxose, xylose and arabinose, and most preferably being ribose, deoxyribose or arabinose, is esterified to the phosphate moiety at the 5′-position and covalently bonded to the heterocyclic moiety at the 1′-position to form a nucleoside, provided that the sugar is not ribose or deoxyribose when the heterocyclic is cytosine or adenine.

The monovalent heterocyclic ring substituents found suitable for use generally contain 5–10, preferably 6–10 ring atoms, of which 1–4, preferably 1 or 2 are oxygen, nitrogen or sulfur heteroatoms. The ring may be non-hydrogenated, as with imidazolyl, thiazolyl and the like; partially hydrogenated as with imidazolinyl, oxazolinyl, thiazolinyl and the like; or completely hydrogenated as with piperazinyl, morpholino, tetrahydropyrimidinyl and the like.

Suitable heterocyclic moieties can be those derived from a five member heterocyclic ring containing a single heteroatom such as furyl, thienyl or pyrrolyl; a five member heterocyclic ring containing two heteroatoms such as pyrazolyl, imidazolyl, oxazolyl, oxazolinyl, isoxazolyl, isoxazolinyl, thiazolyl and thiazolinyl; a five member ring containing three heteroatoms such as triazolyl, oxadiazolyl, thiadiazolyl, dioxazolyl and oxathiazolyl; or a five member ring containing four heteroatoms such as tetrazolyl, oxatriazolyl, thiatriazolyl and the like.

Suitable heterocyclic moieties for the purposes of this invention can also be those derived from six member heterocyclic rings containing a single heteroatom such as pyridyl, pyranyl, tetrahydropyridyl and the like; a six member ring containing two heteroatoms such as thiopyranyl, dioxinyl, pyridazinyl, pyrazinyl, piperazinyl, oxazinyl, morpholino, pyrimidinyl, dihydropyrimidinyl, tetrahydropyrimidinyl and the like; or a six member ring containing three heteroatoms such as triazinyl, oxathiazinyl, oxadiazinyl and the like.

Suitable heterocyclic groups can also be those which are derived from fused heterocyclic rings containing one or two six-membered rings fused to a five-membered ring wherein the six-membered ring(s) is preferably interrupted by two nitrogen atoms and wherein the five-membered ring contains one or two, preferably two nitrogen or sulfur heteroatoms, such as purine, triazolopurine and the like.

Preferred heterocyclic bases for the compounds of the present invention include cytosine, uracil, thymine, adenine, guanine, dihydrouracil, 5-fluorouracil, 5-azauracil, 6-azauracil, 5-azacytosine, 6-azacytosine, tetraphydropyridine dione, 2-amino tetrahydropyridine dione, 6-mercaptopurine, thioguanine, selenoguanine, 8-azaadenine, 7-carboxamide, N-methyl, 2-amino-1, 2, 4-triazolopurine and analogues thereof.

Some compounds of this invention which contain a center of asymmetry may be ordinarily obtained in the racemic form. Their optical isomers can be synthesized from the optically pure glycerol derivatives (D and L). However, such racemates can be separated into their optical antipodes in accordance with any one of many suitable methods known in the art, such as chemical separation. According to one separatory procedure, diastereomers are formed from the racemic mixture by reaction with an optically active auxiliary agent, i.e., an optically active base can be reacted with the phosphate groups or an optically active acid with the amino groups of the compounds of this invention. For example, diasteromeric salts of compounds with free phosphate groups can be formed with optically active amines such as quinine, cinchonidine, brucine, hydroxyhydrinidiamine, morphine, 1-phenylethylamine, 1-naphthylethylamine, phenyloxynaphthylmethylamine, quinidine or basic amino acids such as arginine, lysine and amino acid esters. Diatereomeric salts of basic compounds can be formed with optically active acids such as (+) and (−)-tartaric acid, dibenzoyl (+) and (−)-tartaric acid, diacetyl-(+) and (−)-tartaric acid, camphoric acid, betacamphorsulfonic acid, (+) and (−)-mandelic acid (+) and (−)-malic acid, and the like. Similarly, ester distereomers can be produced by the esterification of compounds containing a free carboxyl group with optically active alcohols such as borneol, menthol, 2-octanol and the like. The resultant mixtures of diasteromeric salts and/or esters can be separated by, e.g. selective crystallization and the desired optically active compounds produced by hydrolytic separation of the isolated diasteromeric compound.

A basic compound of the present invention can be converted into the acid addition salt via reaction with acid, both organic and inorganic, such as aliphatic, alicyclic, araliphatic, aromatic and heterocyclic mono- and polybasic acids, sulfonic acids, and the well known mineral acids. Exemplary of suitable, physiologically acceptable salt forming acids are aliphatic, alicyclic, araliphatic, aromatic, heterocyclic, mono and polybasic carboxylic and sulfonic acids, exemplary of which are formic, acetic, propionic, pivalic, diethylacetic, oxalic, malonic, succinic, maleic, lactic, tartaric, malic, aminocarboxylic, sulfamic, benzoic, salicylic, phenylpropionic, citric, gluconic, ascorbic, nicotinic, isonicotinic methanesulfonic, p-toluenesulfonic, sulfuric, nitric, hydrohalic and phosphoric acids.

Due to their cytotoxic, antineoplastic and immunopotentiating activity, the compounds of this invention are useful as antineoplastic, antiviral and antibacterial agents, particularly antileukemic agents.

The compounds of this invention are effective against the same kinds of cell growth as their corresponding nucleoside or base parent compounds and exhibit a significant improvement on therapeutic indices of the parent compounds with the additive or even synergistic effects from the parent compound and the thiophospholipid moiety.

It can be seen from the generic formula that a number of innovations may be tailored into the parent molecular structure, including:

(a) utilization of any combination of single or multispecies fatty chains varying in length and degree of unsaturation;

(b) replacement of thioether functions by thioester, amide and the like;

(c) differing configurations at the asymmetric lipid carbon, such as the R isomer, the S isomer or racemic (RS) isomers;

(d) variations in the phosphate ester portion;

(e) variations in the sugar moiety of the compounds;
(f) variations in the heterocyclic moiety
(g) inclusion of a halogen atom in lieu of the fatty acid ester or ether at the glycerol -2 position.

The physiochemical and metabolic properties of the compounds can be markedly altered by structural modifications in the nature of the heterocyclic, sugar or nucleoside (heterocyclic+sugar) stereochemistry. As can be appreciated, the cytotoxic nucleotide thiophospholipid analogues, as intact molecules, cannot be properly considered as merely derivatives or forms of existing thiophospholipids or anticancer nucleotides, but rather are a distinct class of compounds.

The compounds of the present invention can be prepared from the starting reactants which themselves are known or can be prepared by methods known to the art. The synthesis of the compounds involve adaptions of reactions of multi species thiophosphatidic acid with nucleotide morpholidates. Thiophosphatidic acids can be prepared by total chemical synthesis utilizing 1-thioglycerol as described in Example 1.

Nucleotides in general are prepared from corresponding nucleosides by direct phosphorylation using $POCl_3$ and trialkyl phosphate(s). This process has been employed to prepare the 5'-phosphates of cytosine arabinoside and 5-fluoro-2'-deoxyuridine in good yields (60-70 percent, pure) from the corresponding nucleosides. Conversion of nucleotides to morpholidates has been achieved in excellent yields, about 95 percent. Synthesis utilizing protecting groups or other phosphorylating reagents can be employed for the preparation of nucleotide components, such as pyrophosphoryl chloride/m-cresol or o-chlorophenol; di(2-t-butyl-phenyl)-phosphorochloridate; cyanoethyl phosphate; 2,2-trichloroethyl-phosphorodichloridate; 2,2,2-trichloro-ethyl-2-chlorophenyl phosphorochloridate; and dinitrobenzyl phosphorochloridate. The direct phosphorylation method is of sufficiently general utility to effectively yield adequate quantities of 5'-nucleotides, even if separation of other minor (2' and/or 3') isomers are required in some instances. This serves to avoid longer synthetic approaches involving protective group chemistry. Chromatographic separation and purification of 5'-monophosphates and final product liponucleotides are then undertaken.

Compounds of this invention, in addition to those set forth in the following examples, include but are not limited to compounds of the generic formula wherein the nucleoside (sugar and heterocyclic) moiety is:
1-β-D-Arabinofuranosylcytosine (ara-C)
5-fluoro-2eoxyuridine (5-FUdR)
5-Azacytidine
9-β-D-Arabinofuranosyladenine (ara-A)
6-Mercaptopurine ribonucleoside; or Tubercidin.

The cytotoxic groups, in addition to the antitumor nucleosides are known or can be prepared by methods known to the art. Such moieties can be conjugated to the thiophosphatidic acids through a phosphoroethyl linkage by mimicking naturally occurring phosphatidyl cholines and ethanolamines.

The compounds can be used in oral, injection and perfusion treatment of cancers in substantially the same manner as the corresponding parent nucleoside or base compound.

The compounds of this invention can be used in admixture with pharmaceutically acceptable organic or inorganic carriers suitable for parental, external or topical applications, it being understood that carriers suitable for use with the present compounds will not react in a deleterious manner with the compounds. Suitable, pharmaceutically acceptable carriers include, but are not limited to, water, salt solutions, alcohols, vegetable oils, polyethylene glycols, gelatin, lactose, amylose, magnesium stearate, talc, silicic acid, paraffins, perfume oils, fatty acid mono and diglycerides, hydroxy alkylcelluloses, polyvinyl pyrrolidone and the like.

The pharmaceutical preparations may also optionally include auxiliary agents such as lubricants, preservatives, stabilizers, wetting agents, emulsifiers, buffers, salts for influence of osmotic pressure, flavoring, coloring and like substances which are nonreactive with the active compounds.

For parental application, particularly useful oily or aqueous sonicated solutions as well as suspensions and emulsions.

Enteric application can be realized by compounding the compounds as tablets, dragees or capsules with carriers and binders of talc, carbohydrate or the like. Sustained release properties may be included by the utilization of differentially degradable coatings such as microencapsulation, multiple coatings or the like.

Generally, the compounds of this invention are dispensed in unit dosage form comprising about 1–3,000 mg of pharmaceutical carrier per each unit dosage with the amount of active compound per unit dosage being on the order of from about 1 mg to about 200 mg.

As topical applications, the compounds are employed in compositions having consistencies ranging from viscous to solid non-sprayable utilizing pharmaceutically acceptable carriers commonly used in topical applications. Suitable formulations include but are not limited to solutions, suspensions, creams, ointments, emulsions, powders, liniments, salves and the like which may include such auxiliary agents as preservatives, stabilizers, wetting agents, buffers and the like.

Sprayable aerosol formulations incorporating the active compounds of this invention are also within the purview of topical application, the active compound preferably in combination with a solid or liquid inert carrier packaged in a suitable dispensing container, pressurized by means of a volatile, normally gaseous propellant, such as freon and the like.

In topical formulations, the active compounds of this invention are utilized at concentrations of from about 0.01 to about 20 percent by weight.

The novel compounds of the present invention are generally administered to animals, including but not limited to mammals and birds with a cytotoxically effective daily dosage of the active compound from about 10 to about 100 mg. administered singly or as divided dosages.

It is to be appreciated that the actual preferred and effective amounts of the compounds of this invention used will vary according to the specific compound being utilized, the particular compositions formulated, the application mode, as well as the particular sites and organism being subjected to treatment. Factors which generally tend to modify drug action will be taken into consideration by those of skill in the art, such factors as age, weight, sex, diet, times and methods of administration, reaction sensitivities, severity of the condition treated, etc. Optimal application rates for any given set of conditions can be determined by those skilled in the art employing conventional dosage determination tests, considering the foregoing guidelines.

The following specific embodiments are set forth to illustrate the preparation and use of the compounds of the present invention and are not to be construed as limitative. Unless otherwise indicated, all parts and percentages are by weight.

Melting points were determined in capillary tubes on Mel-Temp apparatus and NMR spectra were obtained with a Varian XL-100 spectrometer using $Me_4Si$ as an internal standard.

EXAMPLE 1

1-β-D-Arabinofuranosylcytosine-5'-diphosphate-rac-1-S-hexadecyl-2-0-palmitoyl-1-thioglycerol. (1, ara-CDP-DL-PTCA)

To a mixture of 32.45 g (0.3 mol) of 3-mercapto-1,2-propanediol (DL-1-thioglycerol), 45.8 g (0.15 mol) cetyl bromide, 150 ml methanol and 300 ml hexane was added dropwise 390 ml of 1N KOH/methanol at room temperature over a period of one hour and the reaction mixture stirred at room temperature for two days. The resulting KBr was removed by filtration and the filtrate reduced in volume by evaporation to precipitate a white crystalline rac-1-S-hexadecyl-1-thioglycerol. Filtration and methanol washing produced 48.5 g product (97.2%) mp 70°–72° C., 1H NMR($CDCl_3$)δ0.87(3,t,$CH_3$), 1.23 and 1.93 (28,m 14 $CH_2$), 2.43-2.67 (4,m,—$CH_2$—S—$CH_2$), 3.40-3.87 (3,m,—CH—$CH_2$—O—).

A mixture of 33.3 g (0.1 mol) of this product, 30.67 g (0.11 mol) trityl chloride in 250 anhy. pyridine was refluxed for one day and cooled to room temperature, the solvent then evaporated and traces of pyridine removed by evaporation in the presence of toluene. The residue was dissolved in 500 ml diethyl ether and the ether phase washed with water, saturated $NaHCO_3$ and water, and dried over anhy. $Na_2SO_4$. The organic phase was evaporated to dryness and the residue recrystalized from acetone at −10° C. The product rac-1-S-hexadecyl-3-0-trityl-1-thioglycerol was obtained in 73.8% yield (42.4 g) mp 58°–59° C., 1H NMR ($CDCl_3$)δ0.87(3,t,$CH_3$) 1.23 and 1.57 (28,m,14 $CH_2$), 2.40-2.73 (4,m,—$CH_2$—S—$CH_2$—), 3.19(2,d,J=4.5 Hz, —$CH_2$O—), 3.43-3.97 (1,m—C—CH—C), 6.90-7.47 (15,m,$3C_6H_5$).

To a mixture of 28.75 g (0.05 mol) of this product, 4.74 g (0.06 mol) anhy. pyridine in 100 ml benzene was added dropwise 15.12 g (0.055 mol) palmitoyl chloride at room temperature over a period of 30 min. and the reaction mixture treated at 70°–80° C. overnight. After cooling to room temperature, the mixture was mixed with 500 ml diethyl ether, the organic phase was washed with water, 0.2N $H_2SO_4$ and water, and dried over anhy. $Na_2SO_4$. The syrupy residue was heated gently with 4000 ml 95% ethanol, and stored at room temperatures overnight. The white crystalline product, rac-1-S-hexadecyl-2-0-palmitoyl-3-0-trityl-1-thioglycerol, was obtained on filtration in a yield of 36 g (88.5%) mp 44°–45° C., 1H NMR 0.87(6,dt,$2CH_3$), 1.23 and 1.50 (54,m,$27CH_2$), 2.23-2.78(6,m,$CH_2$—CO—;—$CH_2$—S—$CH_2$), 3.28(2,d,J=4.5 Hz,—$CH_2$—O—), 5.10(1,m,C—CH—C), 6.97-7.47(15,m,$3C_6H_5$).

To a solution of 21 g (0.026 mol) of this product in 200 ml hexane and 100 ml glac. acetic acid was added 0.6 g of $PdO_2$ and 1 g of 10% Pd/C, the mixture was hydrogenated at 30–50 psi at room temperature for 3 days, and the catalyst removed by filtration. The filtrate was cooled at 0°–5° C.

The white crystalline product was the acyl-migrated isomer, rac-1-S-hexadecyl-3-0-palmitoyl-1-thioglycerol, yield 2.63 g (17.7%) with the desired product in the filtrate. The filtrate was evaporated to dryness and the residue recrystallized from 50% ethanol to yield 5.32 g (36%) of rac-1-S-hexadecyl-2-0-palmitoyl-1-thioglycerol. The latter was also obtained in 15–42% yield by removing the trityl group of the above tritylated product with $BF_3/CH_2Cl_2$ at 0° for 40 min. or by refluxing in 80% acetic acid in hexanes for 3 hrs.

A solution of 4.57 g (8 mmol) of the product in 100 ml toluene was added dropwise at 0°–5° C. over a period of 1 hour to a mixture of 1.8 g (1.1 ml, 12 mmol) $POCl_3$, and 1.2 g (12 mmol) triethyl amine in 20 ml hexane, and the reaction mixture stirred at room temperature overnight. After decomposing the excess $POCl_3$ by stirring with 3 ml water, the product was extracted with 200 ml ethyl ether and the ether layer washed with 100 ml cold water. The residue was crystallized from hexane at 0°–5° C. overnight to yield 3.94 g (75.7%) rac-1-S-hexadecyl-2-0-palmitoyl-1-thioglycerol-3-phosphate, mp 80°–85° C., 1H NMR ($CDCl_3$—$CD_3OD$—$D_2O$, 2:3:1) δ0.90 (6,dt,$2CH_3$), 1.27 and 1.58 (54,m,$27CH_2$), 2.17-2.77 (6m,$CH_2$—CO, $CH_2$—S—$CH_2$), 4.17 (2m,$CH_2$—O), 5.10 (2;m;C—CH—C).

To an anhydrous solution of 2.6 g (4.0 mmol) of this product in pyridine (150 ml) was added dry ara-CMP morpholidate 4-morpholine-N,N'-dicyclohexylcarboxamidinum salt 2.4 g (3.5 mmol) prepared by the process detailed in Hong et al. Biochem. Biophys. Res. Comm. 94 1169 (1980). The mixture was stirred at room temperature for 5 days and evaporated to dryness, followed by co-evaporating with toluene to remove the residual pyridine. The residue was stirred with 10% HOAc in $CHCl_3$—MeOH—$H_2O$(2:3:1,150 ml) at room temperature for one hour, followed by the addition of 250 ml $CHCl_3$. Following evaporation to dryness and co-evaporation with toluene, the residue was dissolved in 100 ml $CHCl_3$—MeOH—$H_2O$ (2:3:1) and the solution applied to a DE-52 (acetate form) column (2.5×50 cm, jacked 5° C.) prepacked in water and equilibrated in $CHCl_3$—MeOH—$H_2O$ (2:3:1). The column was eluted with 800 ml $CHCl_3$—MeOH—$H_2O$ (2:3:1) and then with a linear gradient of 0–0.15 M ammonium acetate in $CHCl_3$—MeOH—$H_2O$ (2:3:1), 1500 ml each. The fractions between 1200–1800 ml were pooled and quickly evaporated to a small volume at below 30° C., the white solid filtered and washed with 50% aqueous acetone and then with acetone. The solid ($NH_4$ salt of the product) was dissolved in $CHCl_3$—MeOH—$H_2O$ (2:3:1) and the solution was passed through a CG-50 ($Na^+$) column (2.5×10 cm). The column was eluted further with the same solvent (150 ml).

The total eluate was evaporated to dryness and the residue dried in vacuo followed by dissolution in a minimal amount of hexane with acetone added to turbidity. The product as sodium salt was filtered and dried in vacuo over $P_2O_5$, to yield 875 mg (25.0%) mp 195°–200° C. 1H NMR ($CDCl_3$—$CD_3OD$—$D_2O$ 2:3:1)δ0.87 (6,dt,2 $CH_3$), 1.08-1.70 (54,m,27 $CH_2$), 2.13-283 (6,m,$CH_2$—CO, $CH_2$—S—$CH_2$), 3.84-4.50 (m,H2',H3',H4',H5', $CH_2O$), 5.05 (1,m, C—CH—C), 5.91 (1,d, J=7.5 Hz, cytosine H5), 6.08 (1,d, J=5.2 Hz, H1'), 7.78 (1,d, J=7.5 Hz, cytosine H6).

EXAMPLE 2

1-β-D-Arabinofuranosylcytosine-5'-diphosphate-rac-1-S-octadecyl-2-0-palmitoyl-1-thioglycerol (ara-CDP-D,L-PTBA)

Using the process of Example 1, this compound was prepared by substituting stearly bromide for cetyl bromide, the product having a mp 190°–195° C., $^1$H NMR (CDCl$_3$—CD$_3$OD—D$_2$O, 2:3:1)δ0.92 (6,dt, J=6 Hz, 2CH$_3$), 1.30–1.77 (58,m,29 CH$_2$), 2.25–2.82 (6,m, CH$_2$—CO, CH$_2$—S—CH$_2$), 3.93–4.58 (m, HDO, H2',H4',H5', CH$_2$O), 4.98–5.18 (1,m,C—CH—C), 5.94 (1,d, J=7.5 Hz, cytosine H$_5$), 6.11 (1,d, J=5.2 Hz, H1') 7.84 (1,d, J=7.5 Hz, cytosine H6).

EXAMPLE 3

The results of antitumor evaluations carried out are presented in Tables 1 and 2. The results indicate that the thio derivatives of the present invention have produced a significant increase in life span of L1210 tumor-bearing mice.

In conducting the evaluations, the activity was tested against i.p. implanted L1210 leukemia in mice. In conducting the tests, the ascites form of L1210 lymphoid leukemia (L1210/0) and deoxycytidine kinase deficient ara-C resistant L1210 leukemia (L1210/ara-C), grown in DBA/2J mice, were employed. The assay was performed according to the National Cancer Institute (NCI) protocol 1.100, described by R. I. Geran et al., Cancer Chemother. Rep. (Part 3) 3(2), 7, 47 (1972).

Intraperitoneal implantations of $1 \times 10^6$ cells ($1 \times 10^5$ cells for L1210/ara-C) in 0.1 ml suspension to the control and the treated groups was carried out using donor mice (DBA/2J) bearing 5 day tumor cells. Each group consisted of six DBA/2J male mice. The conjugates were dissolved in 0.9% NaCl by sonification with a Biosonik sonicator at maximum power, and 0.5 ml of the solution was administered i.p. once daily. Control animals received a 0.5 ml injection of normal saline. Testing was followed as described in the NCI protocol and evaluation by comparison of median survival time (ST) of the treated animals (T) to that of the control animals (C) by the percentage increase in life span (% ILS) [median ST(T)/median ST(C)−1]×100 (%).

Table 1 summarizes the results obtained against L1210/0 by i.p. treatments with ara-C, its two reference lipophilic prodrugs (5'-0-palmitoyl-and N$^4$-palmitoyl-ara-C), ara-CDP-L-dipalmitin, ara-CDP-1-0-alkyl-phospholipid conjugates and thio analogs, ara-CDP-DL-PTCA (1-β-D-arabinofuranosylcytosine-5'-diphosphate-rac-1-S-hexadecyl-2-0-palmitoyl-1-thioglycerol) and ara-CDP-DL-PTBA (1-β-D-arabinofuranosylcytosine-5'-diphosphate-rac-1-S-octadecyl-2-0-palmitoyl-1thioglycerol) at the optimal doses on the two treatment schedules, i.e., qd 1 and qd 1–5.

The untreated mice died on days 7–8 after tumor implantation. Under a treatment regimen of daily injection of ara-C for 5 days the maximum activity was obtained at 200 mg (822 μmole)/kg/day and the ILS value was 129%. With treatment by ara-CDP-DL-PCA and ara-CDP-DL-PBA at their optimum dosages (80 and 100 mg, 80 and 99 μmole/kg/day) for 5 days, the ILS values were measured at 264 and 229%, respectively. However, the thio analogs, ara-CDP-DL-PTCA and ara-CDP-DL-PTBA exhibited remarkable ILS values of 379 and 371% respectively at 80 mg (80 and 78 μmol)/kg/day for 5 days with one 45 day survivor each. Thus, ara-CDP-DL-PTCA and -PTBA were 3 times more effective than ara-C with only one-tenth of the molar dose of ara-C. The average weight loss of the animals provided preliminary indications that toxicity was less than that of ara-C. They also showed a strong activity with a single dose treatment of 400 mg (400 and 389 μmole)/kg/day each (ILS, 293 and 307%, respectively, with one 45 day survivor each), while reference depot forms of ara-C, 5'-0-palmitoyl- and N$^4$-palmitoyl-ara-C produced ILS values of 150 and 179% respectively at 200 mg (415 μmole)/kg/day.

Ara-CDP-L-dipalmitin and the oxygen analogs, ara-CDP-DL-PCA and -PBA, with the same dosage, provided ILS of 194, 293 and 257%, respectively. Thus, under the treatment system, the new thio analogs of the present invention were found to be much more effective than the oxygen analogs, ara-CDP-L-dipalmitin and the reference prodrugs.

Table 2 summarizes the results obtained by i.p. treatments of deoxycytidine kinase deficient ara-C resistant L1210(1210/ara-C) with the compounds at the optimal dosages on the treatment schedules. The untreated mice died on days 8–11 after tumor cell implantation. Under a treatment regimen of daily injection of the optimal dose (60 mg, 247 μmole)/kg/day of ara-C for 5, 9 and 15 days, the maximal value achieved were 56, 82 and 147%, respectively, indicating that this particular L1210/ara-C subline was not completely deficient in deoxycytidine kinase. However, the novel thio derivatives of this invention exhibited a remarkable antitumor activity. With treatment by ara-CDP-DL-PTCA and-PTBA at their optimal doses (60 and 80 mg, 60 and 78 μmole/kg/day) the ILS values found as of 45 days were >356 and >400%, respectively. A single dose treatment with the conjugates exhibited more remarkable activity. Since more than 3 out of 6 mice survived over 45 days, the ILS' could not be determined except the values as of day 45. Most of the animals survived more than 80 days. Ara-CDP-DL-PTCA produced 6 of 6 45 day survivors with 4 of 6 80 day survivors. The novel thio analogs were found to be much more effective than the oxygen analogs, ara-CDP-L-dipalmitin and the reference prodrugs, 5'-0-palmitoyl-ara-C and N$^4$-palmitoyl-ara-C, being much more effective than ara-C with only one tenth of the total molar dose of ara-C (15 day treatment).

From the foregoing description, one skilled in the art to which this invention pertains, can easily ascertain the essential features thereof, and can make various changes and modifications to adapt it to various usages and conditions without departing from the spirit and scope thereof.

TABLE 1

| | | | | | Survival days | | | |
|---|---|---|---|---|---|---|---|---|
| Compound | Treatment schedule (qd) | Active dose range[b] mg(μmole)/kg/day | Optimal dose[c] mg(μmole)/kg/day | Wt change (g/mouse) on day 8 | range | median (T/C) | % ILS[d] | 45-day Survivors |
| ara-C | 1 | | 400(1644) | +3.58 | 8–10 | 8.0/7.0 | 14 | 0 |
| | 1–5 | 5.00(20.6)–350(1439) | 200(822) | −2.90 | 15–17 | 16.0/7.0 | 129 | 0 |
| ara-CDP-DL-PTCA.2Na | 1 | 300(300)–400(400) | 400(400) | −0.33 | 16–>45 | 27.5/7.0 | 293 | 1 |

Antitumor activity against i.p. inoculated L1210/0 leukemic mice[a].

TABLE 1-continued

Antitumor activity against i.p. inoculated L1210/0 leukemic mice[a].

| Compound | Treatment schedule (qd) | Active dose range[b] mg(μmole)/kg/day | Optimal dose[c] mg(μmole)/ kg/day | Wt change (g/mouse) on day 8 | Survival days range | median (T/C) | % ILS[d] | 45-day Survivors |
|---|---|---|---|---|---|---|---|---|
|  | 1–5 | 60.0(60.0)–80.0(80.0) | 80.0(80.0) | −0.66 | 25–>45 | 33.5/7.0 | 379 | 1 |
| ara-CPD-DL-PTBA.2Na | 1 | 200(195)–400(389) | 400(389) | +0.72 | 23–>45 | 28.5/7.0 | 307 | 1 |
|  | 1–5 | 40.0(38.9)–80.0(77.8) | 80.0(77.8) | −2.53 | 29–>45 | 33.0/7.0 | 371 | 1 |
| ara-CDP-DL-PCA.2Na | 1 | 300(305)–400(407) | 400(407) | +1.47 | 20–33 | 27.5/7.0 | 293 | 0 |
|  | 1–5 | 40.0(40.7)–80.0(81.3) | 80.0(81.3) | +0.33 | 21–30 | 25.5/7.0 | 264 | 0 |
| ara-CDP-DL-PAB.2Na | 1 | 300(294)–500(490) | 400(392) | −1.00 | 15–29 | 25.0/7.0 | 257 | 0 |
|  | 1–5 | 60.0(58.8)–100(97.9) | 100(97.9) | −0.95 | 18–32 | 23.0/7.0 | 229 | 0 |
| ara-CDP-L-dipalmitin.2Na | 1 | 50.0(48.9)–400(391) | 400(391) | −1.60 | 8–31 | 23.5/8.0 | 194 | 0 |
|  | 1–5 | 10.0(9.80)–80.0(78.2) | 40.0(39.1) | −1.90 | 24–<45 | 30.0/8.0 | 275 | 1 |
| 5′-O—palmitoyl-ara-C | 1 | 100(208)–250(519) | 200(415) | +2.00 | 12–<45 | 17.5/7.0 | 150 | 1 |
| N[4]—palmitoyl-ara-C | 1 | 100(208)–250(519) | 200(415) | −0.50 | 14–23 | 19.5/7.0 | 179 | 0 |

[a]Each group of 6 DBA/2J mice (wt. 20–25 g) received i.p. inoculation of 1 × 10[6] cells on day 0. Treatments (i.p.) were initiated 24 hr after tumor inoculation. Animals were observed daily until death or 45 days.
[b]Tested doses producing an increase in life span ≧25% over the controls.
[c]Dose producing greatest increase in life span.
[d]Percentage increase in life span: (T/C − 1) × 100.

TABLE 2

Antitumor activity against i.p. inoculated L1210/ara-C leukemic mice[a].

| Compound | Treatment schedule (qd) | Active dose range[b] mg(μmole)/kg/day | Optimal dose[c] mg(μmole)/ kg/day | Wt change (g/mouse) on day 8 | Survival days range | median (T/C) | % ILS[d] | 45-day Survivors |
|---|---|---|---|---|---|---|---|---|
| ara-C | 1 |  | 200(822) | +3.60 | 9–12 | 10.5/9.5 | 17 | 0 |
|  | 1–5 | 10.0(41.1)–100(411) | 60.0(24) | +0.03 | 14 | 14.0/9.0 | 56 | 0 |
|  | 1–9 |  | 60.0(247) | −1.80 | 15–18 | 15.5/8.5 | 82 | 0 |
|  | 1–15 |  | 60.0(247) | −0.93 | 17–21 | 21.0/8.5 | 147 | 0 |
| ara-CDP-DL-PTCA.2Na | 1 | 200(200)–400(400) | 300(300) | +0.30 | — | >45.0/9.0 | >400[e] | 6 |
|  | 1–5 | 40.0(40.0)–80.0(80.0) | 60.0(60.0) | −0.98 | 29–>45 | >41.0/9.0 | >356[e] | 3 |
| ara-CDP-DL-PTBA.2Na | 1 | 200(195)–500(486) | 400(389) | +0.45 | 29–>45 | >45.0/9.0 | >400[e] | 4 |
|  | 1–5 | 40.0(38.9)–80.0(77.8) | 80.0(77.8) | −1.03 | 25–>45 | >45.0/9.0 | >400[e] | 4 |
| ara-CDP-DL-PCA.2Na | 1 | 100(102)–600(610) | 400(407) | +0.47 | 22–>45 | 29.5/9.0 | 228 | 1 |
|  | 1–5 | 20.0(20.3)–120(122) | 80.0(81.3) | −0.32 | 22–38 | 30.0/9.0 | 233 | 0 |
| ara-CDP-DL-PBA | 1 | 400(413)–500(517) | 400(413) | −2.60 | 25–>45 | 36.0/9.0 | 300 | 2 |
|  | 1–5 | 80.0(82.6)–100(103) | 80.0(82.6) | −2.15 | 30–>45 | >41.0/9.0 | >356[e] | 3 |
| ara-CDP-L-dipalmitin.2Na | 1 | 200(195)–400(391) | 300(293) | −0.70 | 28–>45 | 39.0/9.0 | 333 | 2 |
|  | 1–5 | 20.0(19.5)–60.0(58.7) | 60.0(58.7) | −2.10 | 24–>45 | 34.0/9.0 | 278 | 2 |
| 5′-O—palmitoyl-ara-C | 1 | 50.0(104)–300(623) | 300(623) | −2.80 | 4–>45 | 17.5/9.0 | 94 | 2 |
| N[4]—palmitoyl-ara-C | 1 | 50.0(104)–300(623) | 300(623) | −1.76 | 7–18 | 16.0/10.5 | 52 | 0 |

[a]Each group of 6 DBA/2J mice (wt. 20–25 g) received i.p. inoculation of 1 × 10[5] cells on day 0. Treatments (i.p.) were initiated 24 hr after inoculation. Animals were observed daily until death or 45 days.
[b]Tested doses producing an increase in life span ≧25% over the controls.
[c]Dose producing greatest increase in life span.
[d]Percentage increase in life span: (T/C − 1) × 100.
[e]As of day 45.

What is claimed is:

1. A compound selected from the group of compounds having the formula $$\begin{array}{c} CH_2-A_1-R_1 \\ | \\ X-C-H \quad\quad O \quad\quad O \\ | \quad\quad\quad || \quad\quad || \\ CH_2-A_3-P-A_4-P-A_5-\text{sugar-heterocyclic} \\ | \quad\quad | \\ OH \quad\quad OH \end{array}$$

wherein:
$R_1$ is selected from the group consisting of alkyl and alkenyl containing from about 8 to about 22 carbon atoms;
$A_1$ is S;
$A_3$, $A_4$ and $A_5$ are each O; and
X is fatty acyl containing from about 8 to about 22 carbon atoms;
sugar is arabinose, esterified to the phosphate moiety at the 5′-position and covalently bonded to the heterocyclic moiety at the 1′-position to form a nucleoside;
heterocyclic is cytosine and
physiologically acceptable salts thereof.

2. 1-β-D-arabinofuranosylcytosine-5′-diphosphate-rac-1-S-hexadecyl-2-0-palmitoyl-1-thioglycerol.

3. 1-β-D-arabinofuranosylcytosine-5′-diphosphaterac-1-S-octadecyl-2-0-palmitoyl-1-thioglycerol.

4. A pharmaceutical composition containing from 1 to about 200 mg of a compound as defined by claim 1 in combination with 1 to about 3000 mg of a pharmaceutically acceptable carrier.

* * * * *